United States Patent [19]

Kofsky et al.

[11] 4,086,915
[45] May 2, 1978

[54] EAR OXIMETRY PROCESS AND APPARATUS

[75] Inventors: Harvey I. Kofsky, 3250 Ellendale, Montreal, Quebec; Glenfield Warner, 3010 Matis St., Ville St. Laurent, Montreal H4R 1A3, Quebec, both of Canada

[73] Assignees: Harvey I. Kofsky; Glenfield Warner; Harry Schwartz, Canada

[21] Appl. No.: 689,509

[22] Filed: May 24, 1976

Related U.S. Application Data

[63] Continuation-in-part of Ser. No. 573,106, Apr. 30, 1975, abandoned.

[51] Int. Cl.$^2$ .............................................. A61B 5/00
[52] U.S. Cl. ...................................... 128/2 L; 356/41
[58] Field of Search ............ 128/2 L, 2.05 A, 2.05 D, 128/2.05 M, 2 V; 356/39–41

[56] References Cited

U.S. PATENT DOCUMENTS

| | | | |
|---|---|---|---|
| 2,790,438 | 4/1957 | Taplin | 128/2 L |
| 3,152,587 | 10/1964 | Ullrich et al. | 128/2 L |
| 3,412,729 | 11/1968 | Smith, Jr. | 128/2 L |
| 3,638,640 | 2/1972 | Shaw | 128/2 L |
| 3,658,480 | 4/1972 | Kane et al. | 356/39 X |
| 3,714,372 | 1/1973 | Rosen et al. | 356/39 X |
| 3,847,482 | 11/1974 | Sokol | 356/40 |
| 3,847,483 | 11/1974 | Shaw et al. | 356/41 |
| 3,888,238 | 6/1975 | Meindl et al. | 128/2 V |
| 3,998,550 | 12/1976 | Konishi et al. | 128/2 L X |

OTHER PUBLICATIONS

Cohen et al., "A Light Emitting Diode . . . Oximeter," Med. & Biol. Engng., vol. 10, pp. 385–391, 1972.

Primary Examiner—Robert W. Michell
Assistant Examiner—Lee S. Cohen
Attorney, Agent, or Firm—Spencer & Kaye

[57] ABSTRACT

The invention relates to a non-invasive oximetry process for determining the value of oxygen saturation of the blood of a subject. In some ear oximetry processes, light at two or more frequencies is transmitted through the ear lobe or pinna of the ear of a subject, and the intensity of the transmitted light is measured on the other side of the ear lobe. These processes are affected by such variables as depth of blood in the ear lobe or pinna and differences in the total hemoglobin concentration in the blood. Applicant has discovered that inaccuracies caused by these variables can be eliminated or greatly reduced by taking the derivative of the intensity of the transmitted light, and processing the values of these derivatives in association with a set of predetermined pseudo coefficients by applying these to newly developed relationships disclosed in the specification. The result of such processing yields the value of oxygen saturation of the blood of the subject. An apparatus for carrying out the inventive process is also taught.

21 Claims, 4 Drawing Figures

EAR OXIMETRY PROCESS AND APPARATUS

CROSS-REFERENCE TO RELATED APPLICATIONS

This application is a continuation-in-part of application Ser. No. 573,106, filed Apr. 30, 1975, now abandoned.

BACKGROUND OF THE INVENTION

1. Field of the Invention

This invention relates to a non-invasive method of oximetry in which light contacts an area of skin surface of a subject and is then detected to determine oxygen saturation of the patient's blood, and to an apparatus for carrying out the method. The light which contacts the area can either then pass through the skin of the subject before reaching the detector, or can be reflected from the area to be directed at the detector. More specifically, this invention relates to such a method wherein the rate of change of light intensity is determined to thereby determine oxygen saturation, and to an apparatus for carrying out the method.

2. Statement of the Prior Art

Oximetry methods are used to determine oxygen saturation of a subject's blood, i.e., the percentage of oxygenated hemoglobin in the blood. Such methods may be of the invasive or the non-invasive types. The non-invasive type can be further subdivided into a transmittance method, and a reflectance method. With both the transmittance and reflectance method, a source of light is directed at an area of skin surface of the subject. In the transmittance method, the light passes through the skin of the subject and is then detected by the detector. In the reflectance method, the light is reflected by the area and is then directed at the detector.

In presently known methods of ear oximetry, a light source is directed at one side of the ear lobe or pinna (hereinafter referred to as the ear lobe) and a light detector on the opposite side of the ear detects the intensity of light transmitted through the ear lobe or pinna. Oximetry methods are classified a either relative or absolute.

In the relative methods, a reference is necessary, and saturation is determined relative to the reference. As is well known, the amount of light absorbed by the ear as light is transmitted through it is a function of the attenuation due to skin, muscle, fat, cartilage, etc. of the ear as well as the attenuation due to blood in the ear. The attenuation due to blood is itself dependent on the amount of oxygenated hemoglobin in the blood.

In the absolute method, light at two different frequencies is used, and, advantage is taken of the knowledge that the degree of absorption of red light at a certain frequency is different for oxygenated vs. deoxygenated blood. However, as regards infra-red light at a certain frequency, the degree of absorption is the same for both oxygenated and deoxygenated blood. By measuring absorption at red and infra-red light, oxygen saturation can be determined.

One approach of the absolute method is to provide a transducer which can squeeze the ear tightly to provide a "bloodless ear." The amount of light absorbed by the bloodless ear is measured, and the transducer is then adjusted so that the ear is no longer squeezed and blood can once again flow in the ear. Light is again transmitted through the ear lobe under the second condition, and the difference in the amount of light absorbed under the two conditions is used as an indication of the amount of oxygenated hemoglobin in the blood.

This approach has the disadvantages that, no matter how tight the ear lobe is squeezed, there is still some blood left, so that oxygen saturation determined in this fashion may be inaccurate. Further, the approach is clumsy, and therefore not often used, and, in addition, this approach does not take into account the differences of absorption due to differences in the non-blood tissue in the light path.

Other disadvantages of this method are that results may be affected by such variables as the depth of blood in the ear lobe, and differences in total hemoglobin concentration in the blood.

SUMMARY OF THE INVENTION

It is therefore an object of the invention to provide a method of oximetry which overcomes or substantially reduces the above disadvantages.

It is a further object of the invention to provide an apparatus specifically for the purpose of carrying out the invention.

In accordance with the invention, it is the time derivative of the intensity of the transmitted light which is measured to determine oxygen saturation.

More specifically, in accordance with the invention a process for determining the value of oxygen saturation of the blood of a subject comprises: mounting a source of light adjacent the subject such that light from the source is directed at an area of skin surface on the subject; disposing a light detector means relative to said source of light such that light passing from the source to the detector will contact said area; directing a first ray of light at a first frequency at said area; directing a second ray or light at a second frequency at said area; detecting the light intensity of the rays of light after they contact said area to provide electrical signals representative of the light intensities at said first and second frequencies; differentiating said electrical signals representative of the light intensities at said first and second frequencies respectively; providing said differentiated signals to a processor means, said processor means comprising a set of predetermined coefficients; and processing said differentiated signals in association with said predetermined coefficients to obtain said value of oxygen saturation.

Using a reflectance approach, the process consists of:

mounting a source of light such that light from the source is directed at an area of skin surface on the subject to be reflected by said area of skin surface;

disposing a light detector means relative to said area such that light reflected from said area will be directed at said detector;

directing a first ray of light at a first frequency at said area and, thereby, by reflectance, at said detector;

directing a second ray of light at a second frequency at said area and, thereby, by reflectance, at said detector;

detecting the light intensity of the reflected rays of light to provide electrical signals representative of the light intensities at said first and second frequencies;

differentiating said electrical signals representative of the light intensities at said first and second frequencies respectively;

providing said differentiated signals to a processor means, said processor means comprising a set of predetermined coefficients;

and processing said differentiated signals in association with said predetermined coefficients to obtain said value of oxygen saturation.

Using the transmittance approach, the process consists of:

mounting an earpiece on the ear lobe of the subject, the ear piece comprising light directing means and light intensity detecting means and being arranged such that the light directing means is on one side of said ear lobe and the light detecting means is on the other side of said ear lobe. A first ray of light at a first frequency is directed at the light directing means, and a second ray of light at a second frequency is directed at the light directing means, whereby the rays are directed to the ear lobe and transmitted through the ear lobe, and the light intensity of the light transmitted through the ear lobe at the first and second frequency is detected to provide light intensity signals. The light intensity signals of the first and second frequencies respectively are differentiated and provided to a processor means, the processor means comprising a set of predetermined coefficients. The differentiated signals are processed in association with the predetermined coefficients to obtain the value of oxygen saturation.

Preferably, the first and second rays of light are directed at the light directing means in alternating sequence under the control of a multiplexer unit, and the light intensity signals are reconstituted under the control of a demultiplexer in synchronism with the multiplexer.

The light intensity signals will usually comprise a low level AC signal superimposed on a slowly varying high level signal, and the low level AC signal is separated from the high level signal by the steps of: taking samples of the light intensity signals; applying the samples to the positive input terminal of a differential amplifier; simultaneously applying the samples to the input terminal of a low resolution analogue to digital converter and, therefrom, to the input terminal of a digital to analogue converter whereby to obtain a low resolution conversions of said samples; the output of the digital to analogue converter being applied to the negative input terminal of the differential amplifier.

An apparatus in accordance with the invention for determining the oxygen saturation of the blood of a subject and used in association with a source of light and light intensity detecting means the source of light being mounted such that it is directed at an area of skin surface of the subject, the source of light and the light intensity detecting means being arranged relative to each other such that light passing from the source to the detecting means will contact said area, and means in said source of light for transmitting the light at a first frequency and at a second frequency, said detecting means providing electrical signals representative of said light intensitites.

The apparatus comprising:

differentiating means for differentiating said electrical signals representative of said light intensities at said first and second frequencies respectively;

processor means, comprising a set of predetermined coefficients and adapted to process said differentiated signals in association with said predetermined coefficients to obtain said value of oxygen saturation.

The means for directing the rays of light may comprise a first light source and a second light source. The apparatus further includes multiplexer means for activating the light sources in alternating sequence to thereby provide samples at the first and second frequencies at the output of the detector means, and means for reconstituting the samples at the first frequency and the samples at the second frequency to provide a first reconstituted waveform and a second reconstituted waveform respectively, the aforementioned means being in synchronism with said multiplexer.

The means for reconstituting the waveform may further comprise an input buffer amplifier whose input is connected to the output of the light intensity detecting means. The output of the buffer amplifier is connected, in parallel, to the input terminal of a low resolution analogue to digital convertor and to the positive input terminal of a differential amplifier. The output of the analogue to digital convertor is connected to a digital memory device whose output is connected to the input terminal of a digital to analogue convertor, the output of which is connected to the positive terminal of said differential amplifier, and further including timer means connected to the memory device and the digital to analogue convertor, whereby when a total signal is applied to the buffer amplifier, a resolution portion thereof is subtracted from the totals signal in the differential amplifier.

The light directing means may comprise a fiber optic rod, and said light intensity detecting means may comprise a photo transistor.

The apparatus may be used with the reflectance method wherein the sources of light and the detectors are disposed on the same side of the area, and the detectors are disposed so as to receive light reflected from the area.

When used with the transmittance method, the apparatus includes an ear piece for mounting on the ear of the subject, the ear piece consisting of a light directing means and light intensity detecting means and being arranged such that the light detecting means is mounted on one side of the ear lobe and the light directing means is mounted on the other side of the ear lobe.

BRIEF DESCRIPTION OF THE DRAWINGS

The invention will be better understood by an examination of the following description, together with the accompanying drawings in which.

THEORETICAL ANALYSIS OF THE INVENTION

Figure 1:
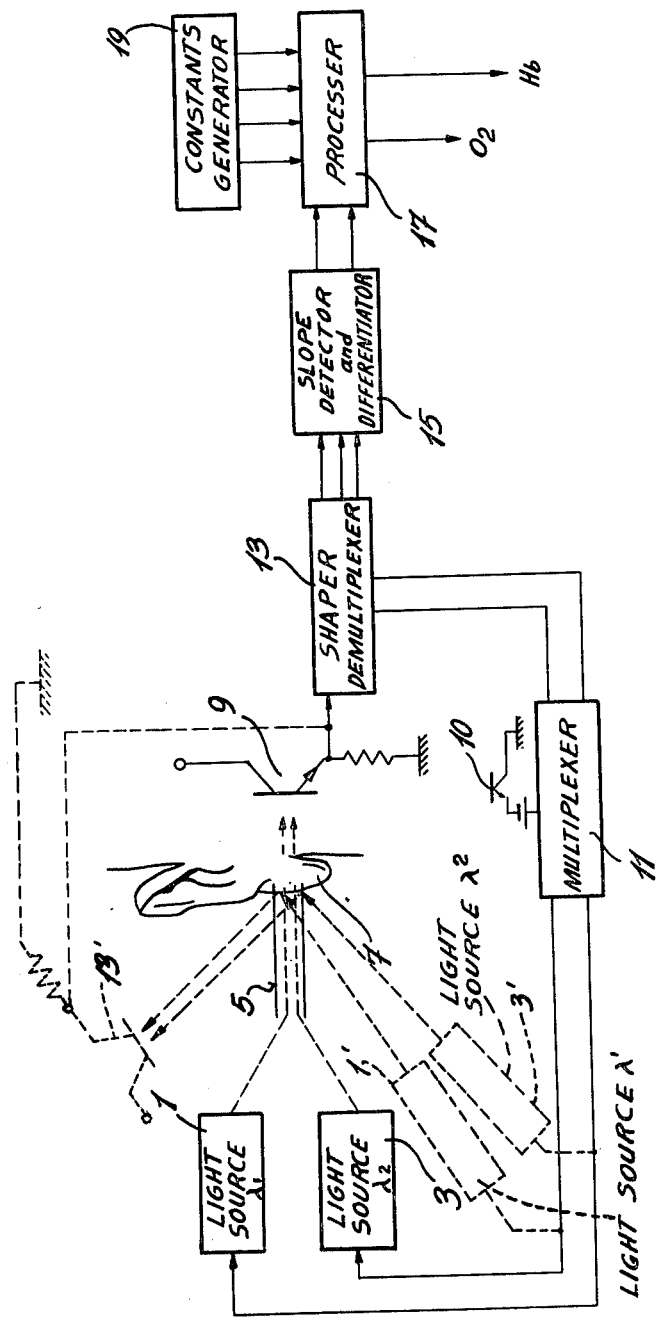
FIG. 1 is a schematic diagram of an electronic ear oximetry apparatus in accordance with the invention.

In the following analysis, it is assumed that, with proper choice of absorption and scattering coefficients, the Lamber-Beer law will apply.

When light rays of wavelengths $\lambda_1$ and $\lambda_2$ are passed through blood containing tissue, such as ear lobes of humans, the following equations apply:

$$D^{\lambda_1} = \alpha_{HbO_2}{}^{\lambda_1} C_{HbO_2}\chi + \alpha_{Hb}{}^{\lambda_1} C_{Hb}\chi - \alpha_T{}^{\lambda_1} l$$

$$D^{\lambda_2} = \alpha_{HbO_2}{}^{\lambda_2} C_{HbO_2}\chi + \alpha_{Hb}{}^{\lambda_2} C_{Hb}\chi - \alpha_T{}^{\lambda_2} l \quad (1)$$

where $D^{\lambda_1}$ = optical density of the transmitted light at wavelength $\lambda_1$ $D^{\lambda_2}$ = optical density of the transmitted light at wavelength $\lambda_2$ $\alpha_{HbO_2}{}^{\lambda_1}$ = attenuation coefficient of HbO$_2$ (oxygenated hemoglobin) at wavelength $\lambda_1$ $\alpha_{HbO_2}{}^{\lambda_2}$ = attenuation coefficient of HbO$_2$ (oxygenated hemoglobin) at wavelength $\lambda_2$ $\alpha_{Hb}{}^{\lambda_1}$ = attenuation coefficient of Hb (hemoglobin) at wavelength $\lambda_1$ $\alpha_{Hb}{}^{\lambda_2}$ = attenuation coefficient of Hb (hemoglobin) at wavelength $\lambda_2$ $^C$HbO$_2$ = concentration of HbO$_2$ per unit volume of blood in the tissue $^C$Hb = concentration of Hb per unit volume of blood in the tissue $\chi$ = length of optical path in blood $l$ = length of optical path in bloodless tissue = constant $\alpha_T{}^{\lambda_1}$ = attenuation coefficient in bloodless tissue at wavelength $\lambda_1$ $\alpha_T{}^{\lambda_2}$ = attenuation coefficient in bloodless tissue at wavelength $\lambda_2$ To simplify the following description we will adopt the following conventions:

Write $\alpha_{HbO_2}$ as $\alpha_O$ and $\alpha_{Hb}$ as $\alpha_H$ and let $C\chi = X$ so that $^C$HbO$\chi = X_O$ and $^C$Hb$\chi = X_H$ then equations (1) can be written as $$D^{\lambda_1} = \alpha_O{}^{\lambda_1}X_O + \alpha_H{}^{\lambda_1}X_H + \alpha_T{}^{\lambda_1} l$$

$$D^{\lambda_2} = \alpha_O{}^{\lambda_2}X_O + \alpha_H{}^{\lambda_2}X_H + \alpha_T{}^{\lambda_2} l \quad (2)$$

Differentiating equations (2) with respect to time, we get:

$$\overset{\circ}{D}{}^{\lambda_1} = \alpha_O{}^{\lambda_1}\overset{\circ}{X}_O + \alpha_H{}^{\lambda_1}\overset{\circ}{X}_H$$

$$\overset{\circ}{D}{}^{\lambda_2} = \alpha_O{}^{\lambda_2}\overset{\circ}{X}_O + \alpha_H{}^{\lambda_2}\overset{\circ}{X}_H$$

Since $l$ is constant, the third term of each equation (2) on the right hand side disappears. Equation (3) can be solved for $\overset{\circ}{X}_O$ and $\overset{\circ}{X}_H$. (See below)

By definition oxygen saturation of the blood =

$$^C\text{HbO}_2/(^C\text{HbO}_2 + {}^C\text{Hb}) \quad (4)$$

since $X = C\chi$ $$\frac{X_O}{X_O + X_H} = \frac{C_{HbO_2}\chi}{C_{HbO_2}\chi + C_{Hb}\chi} = \quad (5)$$

$$\frac{\chi C_{HbO_2}}{\chi[C_{HbO_2} + C_{Hb}]} =$$

$$\frac{C_{HbO_2}}{C_{HbO_2} + C_{Hb}} = \text{oxygen saturation}$$

and Since $\overset{\circ}{X} = C\overset{\circ}{\chi}$ $$\frac{\overset{\circ}{X}_O}{\overset{\circ}{X}_O + \overset{\circ}{X}_H} = \frac{\overset{\circ}{\chi} C_{HbO_2}}{\overset{\circ}{\chi}[C_{HbO_2} + C_{Hb}]} = \quad (6)$$

-continued
$$\frac{C_{HbO_2}}{C_{HbO_2} + C_{Hb}} = \text{oxygen saturation}$$

Solving for $\overset{\circ}{X}_O$ and $\overset{\circ}{X}_H$ from equations (3):

$$\overset{\circ}{X}_O = \frac{\begin{vmatrix} \overset{\circ}{D}{}^{\lambda_1} & \alpha_H{}^{\lambda_1} \\ \overset{\circ}{D}{}^{\lambda_2} & \alpha_H{}^{\lambda_2} \end{vmatrix}}{\begin{vmatrix} \alpha_O{}^{\lambda_1} & \alpha_H{}^{\lambda_1} \\ \alpha_O{}^{\lambda_2} & \alpha_H{}^{\lambda_2} \end{vmatrix}} \quad (7)$$

$$\overset{\circ}{X}_H = \frac{\begin{vmatrix} \alpha_O{}^{\lambda_1} & \overset{\circ}{D}{}^{\lambda_1} \\ \alpha_O{}^{\lambda_2} & \overset{\circ}{D}{}^{\lambda_2} \end{vmatrix}}{\begin{vmatrix} \alpha_O{}^{\lambda_1} & \alpha_H{}^{\lambda_1} \\ \alpha_O{}^{\lambda_2} & \alpha_H{}^{\lambda_2} \end{vmatrix}} \quad (8)$$

$$\frac{\overset{\circ}{X}_O}{\overset{\circ}{X}_O + \overset{\circ}{X}_H} = \quad (9)$$

$$\frac{\begin{vmatrix} \overset{\circ}{D}{}^{\lambda_1} & \alpha_H{}^{\lambda_1} \\ \overset{\circ}{D}{}^{\lambda_2} & \alpha_H{}^{\lambda_2} \end{vmatrix}}{\begin{vmatrix} \overset{\circ}{D}{}^{\lambda_1} & \alpha_H{}^{\lambda_1} \\ \overset{\circ}{D}{}^{\lambda_2} & \alpha_H{}^{\lambda_2} \end{vmatrix} \times \begin{vmatrix} \alpha_O{}^{\lambda_1} & \overset{\circ}{D}{}^{\lambda_1} \\ \alpha_O{}^{\lambda_2} & \overset{\circ}{D}{}^{\lambda_2} \end{vmatrix}} = \text{Oxygen saturation}$$

In equation 9, of the terms on the right hand side, $\overset{\circ}{D}{}^{\lambda_1}$ and $\overset{\circ}{D}{}^{\lambda_2}$ are detected as will be described below. In order to solve the equation, it is necessary to find values for the four attenuation coefficients. In this regard, it is convenient to use pseudo-coefficients which can be found from measurements made on the ear of a suitable subject as discussed below in calibrating an apparatus in accordance with the invention.

In the calibration procedure, an earpiece is placed on the ear of a subject who is breathing ordinary air. Light at wavelengths $\lambda_1$ and $\lambda_2$ is transmitted through the ear lobe of the subject, and optical density readings $\overset{\circ}{D}{}^{\lambda_1}$ and $\overset{\circ}{D}{}^{\lambda_2}$ are taken at the same time as an arterial blood sample is taken. This sample is analysed for oxygen saturation and total hemoglobin concentration, and $C_{HbO_2}{}^{100}$ and $C_{Hb}{}^{100}$ are thence calculated.

The subject is then made to breath air of reduced oxygen content to reduce his arterial blood oxygen saturation to 75%. The above procedure is then repeated to obtain values for $\overset{\circ}{D}{}^{\lambda_1}$, $\overset{\circ}{D}{}^{80}$ 2, $C_{HbO_2}{}^{75}$ and $C_{Hb}{}^{75}$ at 75% saturation.

The following equations will then apply with respect to $\lambda_1$ $$\overset{\circ}{D}_\phi{}^{\lambda_1} = C_{HbO_2}{}^{100} \alpha_O{}^{\lambda_1} \overset{\circ}{\chi}_1 + C_{Hb}{}^{100} \alpha_H{}^{\lambda_1} \overset{\circ}{\chi}_1$$

$$\overset{\circ}{D}_{75}{}^{\lambda_2} = C_{HbO_2}{}^{75} \alpha_O{}^{\lambda_1} \overset{\circ}{\chi}_1 + C_{Hb}{}^{75} \alpha_H{}^{\lambda_1} \overset{\circ}{\chi}_1 \quad (10)$$

Let us define a pseudo-coefficient $$P = \alpha \overset{\circ}{\chi}$$

so that $$\alpha_O{}^{\lambda_1} \overset{\circ}{\chi}_1 = P_O{}^{\lambda_1}$$

and $$\alpha_H{}^{\lambda_1} \overset{\circ}{\chi}_1 = P_H{}^{\lambda_1}$$

Inserting the pseudo-coefficients in equations (10) gives $$\overset{\circ}{D}_{100}{}^{\lambda_1} = C_{HbO_2}{}^{100} P_O{}^{\lambda_1} = C_{Hb}{}^{100} P_H{}^{\lambda_1}$$

$$\overset{\circ}{D}_{75}{}^{\lambda_1} C_{HbO_2}{}^{75} P_O{}^{\lambda_1} + C_{Hb}{}^{75} P_H{}^{\lambda_1} \quad (11)$$

Similarly, for $\lambda_2$ we obtain:

$$\overset{\circ}{D}_{100}{}^{\lambda_2} = C_{HbO_2}{}^{100} P_O{}^{\lambda_2} + C_{Hb}{}^{100} P_H{}^{\lambda_2}$$

$$\overset{\circ}{D}_{75}{}^{\lambda_2} = C_{HbO_2}{}^{75} P_O{}^{\lambda_2} + C_{Hb}{}^{75} P_H{}^{\lambda_2} \quad (12)$$

As the optical densities and the concentrations were measured, we now have four unknowns in four equations, so that numerical values can be obtained for $P_O{}^{\lambda_1}$, $P_H{}^{\lambda_1}$, $P_O{}^{\lambda_2}$ and $P_H{}^{\lambda_2}$.

To show how these pseudo-coefficients can be used in accordance with the invention, we will replace $\alpha\chi$ with $\overset{\circ}{P}X^1$ in equation (3) to obtain:

$$\overset{\circ}{D}{}^{\lambda_1} = P_O{}^{\lambda_1} \overset{\circ}{X}_O{}^1 + P_H{}^{\lambda_1} \overset{\circ}{X}_H{}^1$$

$$\overset{\circ}{D}{}^{\lambda_2} = P_O{}^{\lambda_2} \overset{\circ}{X}_O{}^1 + P_H{}^{\lambda_2} \overset{\circ}{X}_H{}^1 \quad (13)$$

where $\overset{\circ}{X}{}^1 = \overset{\circ}{X}/\overset{\circ}{X}_1$
solving for $\overset{\circ}{X}_O{}^1$ and $\overset{\circ}{X}_H{}^1$ $$\overset{\circ}{X}_O^1 = \frac{P_H^{\lambda_2} \overset{\circ}{D}{}^{\lambda_1} - P_H^{\lambda_1} \overset{\circ}{D}{}^{\lambda_2}}{P_H^{\lambda_2} P_O^{\lambda_1} - P_H^{\lambda_1} P_O^{\lambda_2}} = \frac{a - b}{P_H^{\lambda_2} P_O^{\lambda_1} - P_H^{\lambda_1} P_O^{\lambda_2}} \quad (14)$$

$$\overset{\circ}{X}_H^1 = \frac{P_O^{\lambda_2} \overset{\circ}{D}{}^{\lambda_1} - P_O^{\lambda_1} \overset{\circ}{D}{}^{\lambda_2}}{P_O^{\lambda_2} P_H^{\lambda_1} - P_O^{\lambda_1} P_H^{\lambda_2}} = \frac{c - d}{P_O^{\lambda_2} P_H^{\lambda_1} - P_O^{\lambda_1} P_H^{\lambda_2}} \text{ and} \quad (15)$$

$$\frac{\overset{\circ}{X}_O^1}{\overset{\circ}{X}_H^1 + \overset{\circ}{X}_O^1} = \frac{a - b}{a - b + c - d} \text{ but} \quad (16)$$

$$\frac{\overset{\circ}{X}_O^1}{\overset{\circ}{X}_H^1 + \overset{\circ}{X}_O^1} = \frac{\frac{\overset{\circ}{X}_O}{\overset{\circ}{X}_1}}{\left(\frac{\overset{\circ}{X}_H + \overset{\circ}{X}_O}{\overset{\circ}{X}_1}\right)} = \frac{\overset{\circ}{X}_O}{\overset{\circ}{X}_H + \overset{\circ}{X}_O}$$

From equation (6), we know that this is equal to oxygen saturation. As values for $a$, $b$, $c$ and $d$ are known from calibration (P's) and measurements (D's), it can be seen that oxygen saturation can be determined by both measuring the time derivative of the optical density and using pseudo-coefficients.

The advantages of the inventive method are as follows:

Use of time derivatives eliminates consideration of constant light attenuation in non blood tissue — e.g. skin, muscle, fat, cartilage, blood vessel walls, etc. In this way, the necessity of obtaining bloodless tissue is eliminated.

Use of pseudo coefficients allows calibration directly from subject. In is not necessary to measure optical constants, and only one calibration necessary.

Use of variable $X = C\chi$ makes it unnecessary to know explicitly the sample depth $\chi$ and the hemoglobin concentration $C_i$ of each absorbent.

Errors due to changes in total hemoglobin concentration are reduced or eliminated.

Errors due to changes in ear blood thickness can be reduced.

It is possible that changes in the ear blood thickness from subject to subject may produce errors in oxygen saturation readings. This can be checked by slightly compressing the earpiece on the ear so as to reduce the ear blood volume. If a large enough change in oxygen saturation reading occurs, it will be possible to correct for this if the optical density vs. sample depth curves for whole, non-hemolysed blood are known at the particular wavelengths being used. The changes in ear blood thickness due to cardiac pulsations are small and are not expected to cause errors. It is expected that the pseudo-coefficients $P_i$ will be valid over a wide range of total hemoglobin concentration. However if this error in measured oxygen saturation becomes too great as concentration varies different coefficients $P_i$ can be used for different ranges of total hemoglobin concentration. A set of $P_i$ coefficients can be found at different hemoglobin concentrations such as 3 m moles/liter, 6 m moles/liter, 10 m moles/liter, 13 m moles/liter etc. An estimate of the subjects total hemoglobin concentration can be determined before the oxygen saturation measurements. The set of $P_i$ coefficients most appropriate for the subjects total hemoglobin concentrations is used for the computations. As many sets of $P_i$ coefficients as are necessary for good accuracy can be found. Since these coefficients will be stored in the computer sections of the oximeter, it will be very simple to use them.

It will be appreciated that, although the above analysis dealt with the transmittance case, a similar analysis will be valid for the reflectance case. One skilled in the art would have no difficulties, using a similar approach, in deriving the mathematical formulae for determining the constants in the transmittance case.

As is well known, the derivative of any variable V with respect to time $t$ is given by the expression:

$$\frac{dV}{dt} = \lim_{\Delta t \to 0} \cdot \frac{\Delta V}{\Delta t}$$

As the derivative can be estimated by measuring increments in the variable over an increment of time greater than 0, the $\overset{\circ}{V}$ could, in the above equations, be replaced by the expression $[\Delta V/\Delta t]$; $t > 0$. When this expression is used, it would be increments which are measured rather than derivatives.

DETAILED DESCRIPTION OF THE DRAWINGS

An apparatus for carrying out the method in accordance with the invention is illustrated schematically in FIG. 1. In FIG. 1, the solid lines indicate the transmittance case, whereas the dotted lines indicate the reflectance case. In FIG. 1, rays from light sources 1 and 3, which provide light at frequencies $\lambda_1$ and $\lambda_2$ respectively, are guided by a light guide means, such as a fibre optic rod 5, to the ear lobe 7 of a patient. The light which is transmitted through the ear lobe is detected by a light intensity detector means, such as a photo transistor 9. The light sources are alternately activated by multiplexer 11, which can comprise a timed switching arrangement as well known in the art. As will be appreciated, more than two light sources, each at a different frequency, could be used.

Demultiplexer 13, also under control of the multiplexer 11, is in synchronism with the light sources to reconstitute the wave forms detected by the photo transistor. The shaper demultiplexer circuit is discussed in more detail below in association with FIG. 4 of the drawings.

The output of the demultiplexer is fed to slope detector and differentiator 15. For reasons of accuracy, it is desirous to obtain the slope near the peak of the AC waveform (illustrated in FIG. 2 and discussed below). The slope detector can comprise a differentiating circuit, i.e., an RC circuit. As is well known, when the input to such a circuit is a slope which changes from positive going to negative going, the output of the RC circuit will be a negative going spike at the change over. This spike could then be used to trigger, for example, a flip-flop which could then open, for example an AND gate, to permit the peak value to be applied to a further differentiating circuit whose output provides the derivative of the optical density signal. The derivatives are then applied to processor 17, which is discussed in greater detail below in association with FIG. 3, which also receives an input from constants generator 19. The generator 19 provides values, in the form of current or voltage magnitudes, for the pseudo-coefficients discussed above. This could of course, be either a signal generator or a memory device in the processor with the appropriate values stored therein.

It will, of course, be clear that multiplexing is preferred but not necessary. Thus, the apparatus as illustrated in FIG. 1, but without the multiplexer 11 and the demultiplexer part of 13, would also be useful. In such an apparatus, a measurement would be taken at one light frequency and stored in the processor. A measurement would then be taken at the other frequency and applied to the processor which would now have all the data necessary for computation. Although such an arrangement may not be too practical, it is feasible and therefor within the scope of the instant invention.

Figure 2:
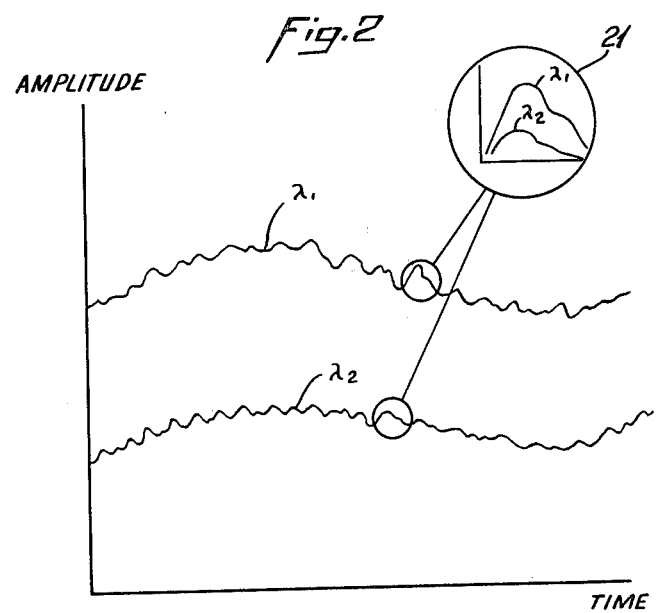
FIG. 2 illustrates typical reconstructed waveforms at the output of the apparatus in FIG. 1.

FIG. 2 shows typical reconstituted waveforms as would appear at the output of 13 in the preferred embodiment. As can be seen, the signal comprises a small AC waveform superimposed on a large value slowly varying DC. The period of the AC waveform is equal to the time between successive beats of the subject's heart. The DC signal is a function of the respiration rate, jaw movement, etc., and is generally a much longer period.

Insert 21 of FIG. 2 is a representation of the AC component of the composite signal. As can be seen, it reaches a peak value at approximately one third of the period.

Figure 3:
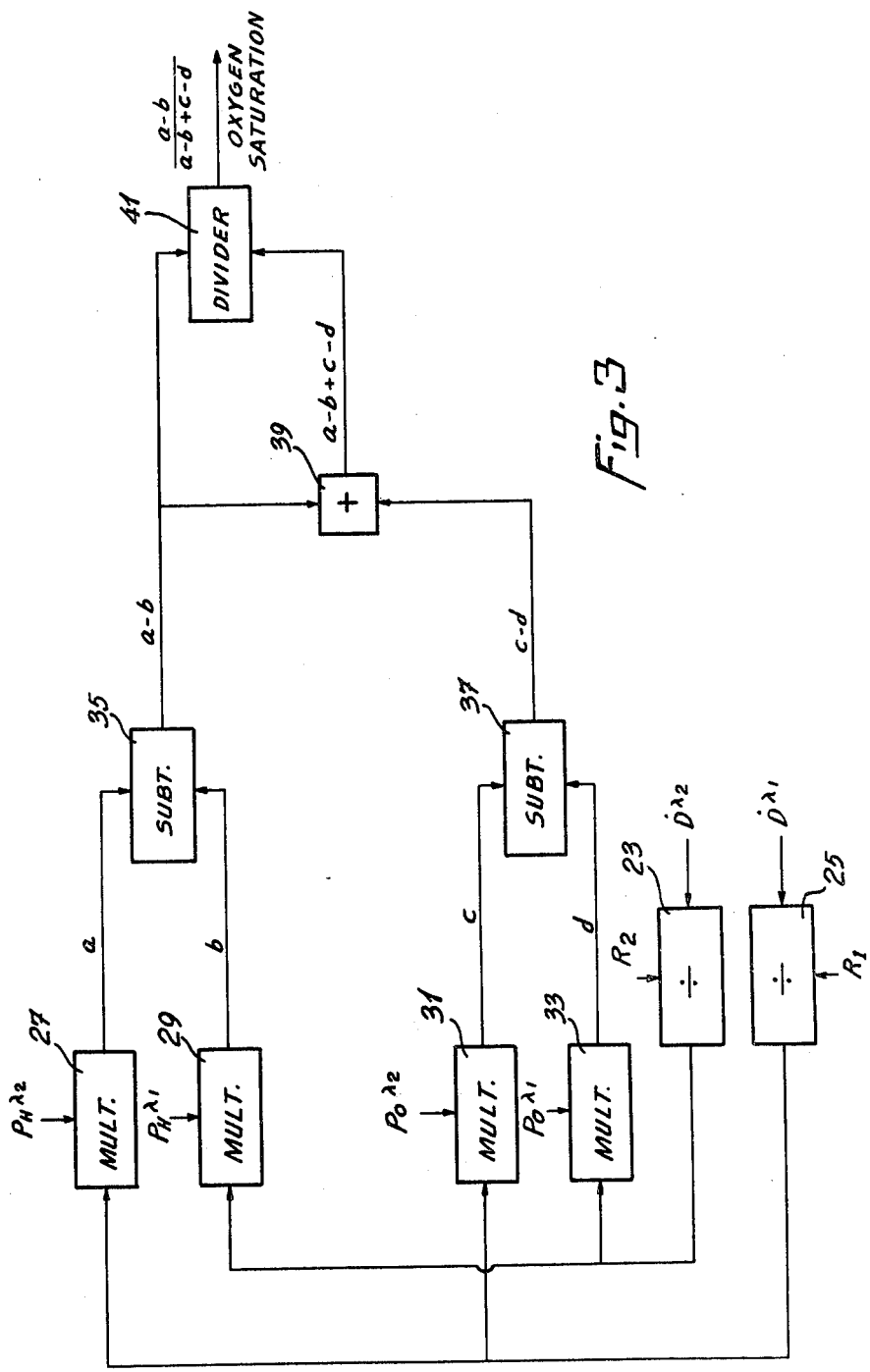
FIG. 3 illustrates, in schematic form, a processor for the apparatus of FIG. 1.

A processor which can be used in the apparatus of FIG. 1 is illustrated schematically in FIG. 3. In FIG. 3, the inputs $\mathring{D}^{\lambda 2}$ and $\mathring{D}^{\lambda 1}$ are fed to dividers 23 and 25 respectively. $R_1$ and $R_2$ are rationalization factors as required. Pseudo-coefficients $P_H^{\lambda 2}$, $P_H^{\lambda 1}$, $P_O^{\lambda 2}$, and $P_O^{\lambda 1}$ are fed to multipliers 27, 29, 31 and 33 respectively, while the output of 23 is fed to 29 and 33, and the output of 25 is fed to 27 and 31. As can be seen from equations 14, 15 and 16 above, the output of 27 is the value $a$, the output of 29 is the value $b$, the output of 31 is the value $c$, and the output of 33 is the value $d$.

The outputs of 27 and 29 are combined in subtractor 35 to provide the value $a-b$, and the outputs of 31 and 33 are combined in subtractor 37 to provide the value $c-d$. These values are combined in adder 39 to provide the value $a-b+c-d$, and this latter value is applied to one terminal of divider 41. The other terminal of 41 is fed with the value $a-b$, so that the output of the divider is the value $a-b/a-b+c-d$, i.e., as seen in equation 16, oxygen saturation.

In order to obtain a reasonable estimate of the slope of the AC component of the waveform in FIG. 2 (the slope of this waveform is, of course, the derivative of the light intensity) it is necessary to amplify this AC component. In order to accomplish this, it is necessary to first remove the DC component as this component constitutes the larger proportion of the total composite signal, and any attempt to amplify the composite signal would lead to amplifier saturation before amplification of the AC component took place.

If there is a constantly large difference between the two frequencies, and if the two frequencies themselves remain within a reasonably narrow band of frequencies, then a low pass filter could be used to remove the DC component. However, in the use of the instant apparatus, the frequencies vary over a wide band and the magnitudes of the frequencies even approach each other, so that this traditional solution is not feasible in the present apparatus.

Figure 4:
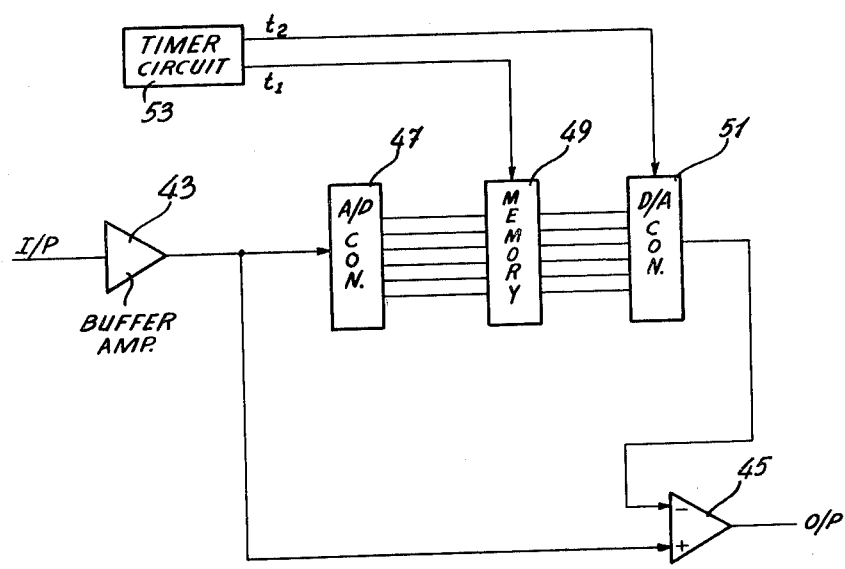
FIG. 4 illustrates an embodiment of the shaper demultiplexer circuit of the apparatus of FIG. 1.

In order to separate out the DC component in this apparatus, applicant has found it necessary to develop a novel circuit, and this circuit is illustrated in FIG. 4 hereof.

Referring to FIG. 4, the circuit comprises a buffer amplifier 43 whose output is fed, in parallel, to the plus terminal of differential amplifier 45 and to the input of analogue to digital convertor (A/D) 47. In the A/D convertor, the amplitude is converted to a digital word which is then stored in memory 49. The output of the memory is converted to an analogue signal in D/A convertor 51 whose output is fed to the negative terminal of amplifier 45.

The circuit is under the control of timer circuit 53.

In the arrangement of FIG. 4, A/D convertor 47 is a low resolution convertor whose resolution is less than the order of amplitude of the small AC component in FIG. 2. Thus, if the AC component is of the order of tenths of volts, then the resolution of 47 would be volts, and if the AC component is of the order of hundredths of volts, then the resolution of 47 could be tenths of volts. (In the latter case, the resolution could also be volts). The advantages of using a low resolution convertor will be immediately apparent as such a low resolution convertor is less expensive and more reliable than a high resolution convertor.

In the operation of the circuit, it is assumed that the low resolution portion of the composite signal is always and entirely due to the DC component. Although this is not rigorously true, use of this assumption in the circuit in accordance with the invention will provide a signal sufficiently indicative of the AC component to be useful in the apparatus of the invention.

In operation, the circuit works as follows:

The combined signal is sent to the input buffer amp. 43 and then to the A/D convertor 47. The signal is also present at the amp. 45. Assuming the AC component is tenths of volts, at the positive terminal the amplitude could be, for example, 2.6 volts. If the resolution of the A/D is volts, the output of the A/D would be 2 volts. This two volts in digital form is stored in memory 49, so that during the next sample time $t_2$ the 2 volt digital word will appear at the input of a D/A convertor 51 and the output of 51 is fed to the negative input of amp. 45.

The 2 volts is subtracted from the combined signal amplitude of the next sample. Thus, if the next sample is 2.5 volts, then the output of 45 will be 0.5 volts. This subtraction essentially separates the large DC value from the composite signal to provide the small AC signal. Amplifier 45 can have its gain set to convert this 0.5 volts to 5 volts for further processing.

The sampling of the signal is under control of the timer 53. At $t_1$ the A/D is caused to convert the composite signal to a digital number. At $t_2$ the digital number is transferred to a memory, so that it will be held constant during the next $t_1$ phase. In essence 47, 49 and 51 comprise a digital sample and hold circuit.

In operation, the apparatus in FIG. 1 works as follows:

An earpiece, which includes the photo transistor 9, is mounted on the ear lobe of a subject. The earpiece also includes the fiber optic rod 5, and the earpiece will be arranged so that the rod is on one side of the ear lobe, preferably the front of the ear lobe, i.e., that side of the ear lobe furthest removed from the neck of the subject, and the light intensity detector is on the other side of the ear lobe, i.e., the back of the ear lobe.

When a reading is required, switch 10 is depressed. This activates the multiplexer 11 which causes the alternate activation of light sources 1 and 3. The light rays from these sources are directed at the ear lobe through rod 5, and the light which is transmitted through the ear is detected by the photo transistor 9 where it is converted to an electrical signal whose amplitude is representative of the light intensity detected by the photo transistor 9. The electrical signals representative of the transmitted light signals, at frequencies $\lambda_1$ and $\lambda_2$ are reconstituted in the demultiplexer 13, and the DC level of these signals is removed in 13 as above described.

The AC levels of the electrical signals are then transmitted to slope detector and differentiator 15 where the signal in the region of the highest part of the slope is differentiated. Thus, we are provided with a derivative electrical signal which is representative of the derivative of the light intensity signal. The derivatives thus obtained are applied to the processor 17 which processes this data together with the coefficients supplied from 19 to provide a value of oxygen saturation at the output.

Returning now to FIG. 1, as can be seen, in the reflectance case, the light sources are disposed relative to an area of skin surface such that the light transmitted from the light sources will be reflected by the area of skin surface. The detector is disposed so that the reflected light will be directed at the detector.

Although in FIG. 1 light in shown as reflected from the ear lobe, it will be appreciated that light may be reflected from any surface area of the skin where good blood volume pulses are obtained. Examples of such areas are the forehead, the fore arm skin, palm of the hand, the foot of a subject or his leg.

After the light is detected, the procedure which is followed is identical to the procedure described above with regard to the transmittance case.

As will be appreciated, the constants for the reflectance case may be different from those of the transmittance case. However, as above mentioned, one skilled in the art would be quite capable of working the mathematical formula needed to derive the constants, and the obtaining of the numerical values will present no problem when the mathematical formula have been derived.

Although apparatus have been illustrated, this was for the purpose of describing, but not limiting, the invention. Various modifications, which will come readily to the mind of one skilled in the art, are within the scope of the invention as defined in the appended claims.

We claim:

1. A process for determining the value of oxygen saturation of the blood of a subject, comprising:
    mounting an earpiece on the ear lobe of the subject, said earpiece comprising light directing means and light intensity detecting means and being arranged such that the light directing means is on one side of said ear lobe and the light detecting means is on the other side of said ear lobe;
    directing a first ray of light, from a first light source, at a first frequency at said light directing means;
    directing a second ray of light, from a second light source, at a second frequency at said light directing means;
    whereby said rays are directed, by said light directing means, to said ear lobe and transmitted through said ear lobe, and the light intensities of the light rays transmitted through the ear lobe at said first and second frequencies are detected, by said light detecting means, and converted, in said light detecting means, to electrical signals representative of said light intensities;
    differentiating, with a differentiating means, said electrical signals representative of said light intensities of said first and second frequencies respectively;
    providing said differentiated signals to a processor means, said processor means comprising a set of predetermined coefficients;
    and processing, in said processor means, said differentiated signals in association with said predetermined coefficients to obtain said value of oxygen saturation.

2. A process as defined in claim 1 wherein said first and second rays of light are directed at said light directing means in alternating sequence under the control of a multiplexer unit;
    and wherein said electrical signals are reconstituted under the control of a demultiplexer in synchronism with said multiplexer.

3. A process as defined in claim 1 wherein said electrical signals comprise a low level AC signal superimposed on a slowly varying high level signal, wherein said low level AC signal is separated from said high level signal by the steps of:
    taking samples of said electrical signals;
    applying said samples to the positive input terminal of a differential amplifier;
    simultaneously applying said samples to the input terminal of a low resolution analogue to digital converter and, therefrom, to the input terminal of a digital to analogue converter whereby to obtain a low resolution conversions of said samples;
    the output of said digital to analogue converter being applied to the negative input terminal of said differential amplifier;
    wherein said low level AC signal is the only signal which is differentiated with said differentiating means.

4. Apparatus for determining the oxygen saturation of the blood of a subject and used in association with an earpiece for mounting on the ear of the subject, the earpiece comprising light directing means and light intensity detecting means and being arranged such that the light detecting means is mounted on one side of the ear lobe and the light directing means is mounted on the other side of the ear lobe, and means for directing rays of light at a first frequency and rays of light at a second frequency at said light directing means whereby said rays are directed at the ear lobe and transmitted through the ear lobe and the light intensity of the light transmitted through the ear lobe at said first and second frequencies is detected to provide electrical signals representative of said light intensities;

said apparatus comprising:

differentiating means for differentiating said electrical signals representative of said light intensities at said first and second frequencies;

processor means, comprising a set of predetermined coefficients and adapted to process said differentiated signals in association with said predetermined coefficients to obtain said value of oxygen saturation.

5. An apparatus as defined in claim 4 wherein said means for directing said rays of light comprises a first light source and a second light source, and further comprising:

multiplexer means for activating said light sources in alternating sequence to thereby provide samples of said electrical signals representative, respectively, of light intensities at said first and second frequencies at the output of said detector means;

and means for reconstituting said samples representative of said first frequency and said samples representative of said second frequency to provide a first reconstituted waveform and a second reconstituted waveform respectively, the aforementioned means for reconstituting said samples being in synchronism with said multiplexer means.

6. An apparatus as defined in claim 5 wherein said means for reconstituting said samples further comprises:

an input buffer amplifier whose input is adapted to be connected to the output of said light intensity detecting means;

a low resolution analogue to digital converter and a differential amplifier, the output of said buffer amplifier being connected, in parallel, to the input terminal of said low resolution analogue to digital convertor and to the positive input terminal of said differential amplifier;

a digital memory device and a digital to analogue converter, the output of said analogue to digital convertor being connected to said digital memory device whose output is connected to the input terminal of said digital to analogue convertor, the output of which is connected to the positive terminal of said differential amplifier;

and timer means connected to said memory device and said digital to analogue convertor;

whereby when a total signal is applied to said buffer amplifier, a resolution portion thereof is subtracted from the totals signal in said differential amplifier.

7. An apparatus as defined in claim 6 wherein said light directing means comprises a fiber optic rod, and wherein said light intensity detecting means comprises a photo transistor.

8. A process for determining the value of oxygen saturation of the blood of a subject, comprising:

mounting a source of light adjacent the subject such that light from the source is directed at an area of skin surface on the subject;

disposing a light detector means relative to said source of light such that light passing from the source to the light means detector will contact said area;

directing a first ray of light, from said source of light, at a first frequency at said area;

directing a second ray of light, from said source of light, at a second frequency at said area;

detecting, with said light detector means, the light intensity of the rays of light after they contact said area to provide electrical signals representative of the light intensities at said first and second frequencies;

differentiating, with a differentiating means; said electrical signals representative of said light intensities of said first and second frequencies respectively;

providing said differentiated signals to a processor means, said processor means comprising a set of predetermined coefficients;

and processing, with said processor means, said differentiated signals in association with said predetermined coefficients to obtain said value of oxygen saturation.

9. A process as defined in claim 8 wherein said first and second rays of light are directed at said area in alternating sequence under the control of a multiplexer unit;

and wherein said electrical signals are reconstituted under the control of a demultiplexer in synchronism with said multiplexer.

10. A process as defined in claim 8 wherein said electrical signals comprise a low level AC signal superimposed on a slowly varying high level signal, wherein said low level AC signal is separated from said high level signal by the steps of:

taking samples of said electrical signals;

applying said samples to the positive input terminal of a differential amplifier;

simultaneously applying said samples to the input terminal of a low resolution analogue to digital converter and, therefrom, to the input terminal of a digital to analogue converter whereby to obtain a low resolution conversions of said samples;

the output of said digital to analogue converter being applied to the negative input terminal of said differential amplifier;

wherein said low level AC signal is the only signal which is differentiated with said differentiating means.

11. A process for determining the value of oxygen saturation of the blood of a subject, comprising:

mounting a source of light such that light from the source is directed at an area of skin surface on the subject to be reflected by said area of skin surface;

disposing a light detector means relative to said area such that light reflected from said area will be directed at said detector means;

directing a first ray of light, from said source of light, at a first frequency at said area and, thereby, by reflectance, at said detector means;

directing a second ray of light, from said source of light, at a second frequency at said area and, thereby, by reflectance, at said detector means;

detecting, with said light detector means, the light intensity of the reflected rays of light to provide electrical signals representative of the light intensities at said first and second frequencies;

differentiating, with a differentiating means, said electrical signals representative of said light intensities at said first and second frequencies respectively;

providing said differentiated signals to a processor means, said processor means comprising a set of predetermined coefficients;

and processing, with said processor means, said differentiated signals in association with said predetermined coefficients to obtain said value of oxygen saturation.

12. A process as defined in claim 11 wherein said first and second rays of light are directed at said area in alternating sequence under the control of a multiplexer unit;

and wherein said electrical signals are reconstituted under the control of a demultiplexer in synchronism with said multiplexer.

13. A process as defined in claim 11 wherein said electrical signals comprise a low level AC signal superimposed on a slowly varying high level signal, wherein said low level AC signal is separated from said high level signal by the steps of:

taking samples of said electrical signals;

applying said samples to the positive input terminal of a differential amplifier;

simultaneously applying said samples to the input terminal of a low resolution analogue to digital converter and, therefrom, to the input terminal of a digital to analogue converter whereby to obtain a low resolution conversions of said samples;

the output of said digital to analogue converter being applied to the negative input terminal of said differential amplifier;

wherein said low level AC signal is the only signal which is differentiated with said differentiating means.

14. A process as defined in claim 11 wherein said area of skin surface comprises the ear lobe of a subject.

15. A process as defined in claim 11 wherein the area of skin surface comprises the forehead of the subject.

16. Apparatus for determining the oxygen saturation of the blood of a subject and used in association with a source of light and light intensity detecting means, the source of light being mounted such that it is directed at an area of skin surface of the subject, the source of light and the light intensity detecting means being arranged relative to each other such that light passing from the source to the detecting means will contact said area, and means in said source of light for transmitting the light at a first frequency and at a second frequency, said detecting means providing electrical signals representative of said light intensities;

said apparatus comprising:

differentiating means for differentiating said electrical signals representative of said light intensities at said first and second frequencies;

processor means, comprising a set of predetermined coefficients and adapted to process said differentiated signals in association with said predetermined coefficients to obtain said value of oxygen saturation.

17. An apparatus as defined in claim 16 wherein said source of light comprises a first light source and a second light source, and further comprising:

multiplexer means for activating said light sources in alternating sequence to thereby provide samples of said electrical signals representative, respectively, of light intensities at said first and second frequencies at the output of said detector means;

and means for reconstituting said samples representative of said first frequency and said samples representative of said second frequency to provide a first reconstituted waveform and a second reconstituted waveform respectively, the aforementioned means for reconstituting said samples being in synchronism with said multiplexer means.

18. An apparatus as defined in claim 17 wherein said means for reconstituting said samples further comprises:

an input buffer amplifier whose input is adapted to be connected to the output of said light intensity detecting means;

a low resolution analogue to digital converter and a differential amplifier, the output of said buffer amplifier being connected, in parallel, to the input terminal of said low resolution analogue to digital convertor and to the positive input terminal of said differential amplifier;

a digital memory device and a digital to analogue converter, the output of said analogue to digital convertor being connected to said digital memory device whose output is connected to the input terminal of said digital to analogue convertor, the output of which is connected to the positive terminal of said differential amplifier;

and timer means connected to said memory device and said digital to analogue convertor;

whereby when a total signal is applied to said buffer amplifier, a resolution portion thereof is subtracted from the totals signal in said differential amplifier.

19. Apparatus for determining the oxygen saturation of the blood of a subject and used in association with a source of light, which source of light directs rays of light at an area of skin surface of the subject for reflection from the area, light intensity detecting means being disposed such that light rays reflected from said area will be directed at said detecting means, means in said source of light for transmitting rays of light at a first frequency and at a second frequency, whereby the light intensity of the light rays reflected from said area at said first and second frequencies is detected to provide electrical signals representative of said light intensities;

said apparatus comprising:

differentiating means for differentiating said electrical signals representative of said light intensities at said first and second frequencies;

processor means, comprising a set of predetermined coefficients and adapted to process said differentiated signals in association with said predetermined coefficients to obtain said value of oxygen saturation.

20. An apparatus as defined in claim 19 wherein said source of light comprises a first light source and a second light source, and further comprising:

multiplexer means for activating said light sources in alternating sequence to thereby provide samples of said electrical signals representative, respectively, of light intensities at said first and second frequencies at the output of said detector means;

and means for reconstituting said samples representative of said first frequency and said samples representative of said second frequency to provide a first reconstituted waveform and a second reconstituted waveform respectively, the aforementioned means for reconstituting said samples being in synchronism with said multiplexer means.

21. An apparatus as defined in claim 20 wherein said means for reconstituting said samples further comprises:

an input buffer amplifier whose input is adapted to be connected to the output of said light intensity detecting means;

a low resolution analogue to digital converter and a differential amplifier, the output of said buffer amplifier being connected, in parallel, to the input terminal of said low resolution analogue to digital convertor and to the positive input terminal of said differential amplifier;

a digital memory device and a digital to analogue converter, the output of said analogue to digital convertor being connected to said digital memory device whose output is connected to the input terminal of said digital to analogue convertor, the output of which is connected to the positive terminal of said differential amplifier;

and timer means connected to said memory device and said digital to analogue convertor;

whereby when a total signal is applied to said buffer amplifier, a resolution portion thereof is subtracted from the totals signal in said differential amplifier.

* * * * *